United States Patent [19]

Thompson

[11] 4,011,313

[45] * Mar. 8, 1977

[54] MEDICAMENT PREPARATIONS

[75] Inventor: Geoffrey F. Thompson, Sunnyvale, Calif.

[73] Assignee: Syntex (U.S.A.) Inc., Palo Alto, Calif.

[ * ] Notice: The portion of the term of this patent subsequent to May 13, 1992, has been disclaimed.

[22] Filed: Oct. 17, 1975

[21] Appl. No.: 623,871

Related U.S. Application Data

[63] Continuation of Ser. No. 477,227, June 7, 1974, abandoned, which is a continuation-in-part of Ser. No. 313,431, Dec. 8, 1972, Pat. No. 3,833,725, and Ser. No. 413,965, Nov. 8, 1973, abandoned.

[52] U.S. Cl. .......................... 424/227; 260/615 B; 424/342; 424/358
[51] Int. Cl.² ................. A61K 31/08; A61K 31/65
[58] Field of Search .................... 424/227, 342; 260/615 B

[56] References Cited

UNITED STATES PATENTS

| | | | |
|---|---|---|---|
| 2,146,324 | 2/1937 | Zellhoefer | 260/615 B |
| 2,271,873 | 2/1942 | Perkins | 260/615 B |
| 2,520,611 | 8/1950 | Roberts | 260/615 B |
| 2,520,612 | 8/1950 | Roberts | 260/615 B |
| 2,943,056 | 6/1960 | Bolt | 260/615 B |
| 3,308,217 | 3/1967 | Lowy | 424/227 X |
| 3,591,641 | 7/1971 | Ameen | 260/615 B |
| 3,629,111 | 12/1971 | Cramer | 252/75 |
| 3,751,562 | 8/1973 | Nichols | 424/227 X |
| 3,833,725 | 9/1974 | Thompson | 424/227 X |
| 3,846,486 | 11/1974 | Marcus | 424/227 X |
| 3,906,043 | 9/1975 | Marcus | 260/559 AT |

FOREIGN PATENTS OR APPLICATIONS

| | | | |
|---|---|---|---|
| 1,296,515 | 5/1962 | France | 260/615 B |
| 1,792,448 | 3/1974 | Germany | 260/615 B |
| 1,203,611 | 8/1970 | United Kingdom | 260/615 B |

OTHER PUBLICATIONS

Lange, Chem. Abs. vol. 69 (1968), p. 99303k.
Agami, Chem. Abs. vol. 69 (1968), p. 76074.

*Primary Examiner*—Albert T. Meyers
*Assistant Examiner*—A. P. Fagelson
*Attorney, Agent, or Firm*—Tom M. Moran; Joseph I. Hirsch

[57] ABSTRACT

A pharmaceutical preparation having a minor amount of a tetracycline medicament, and a major amount of a dialkylated mono- or poly-alkylene glycol vehicle therefor, and, optionally, a minor amount of one or more antioxidants for the dialkylated glycol vehicle. The preparations are stable topical tetracycline formulations having good release and skin penetration characteristics.

23 Claims, No Drawings

MEDICAMENT PREPARATIONS

REFERENCE TO PARENT APPLICATIONS

This application is a continuation of application U.S. Ser. No. 477,227 filed June 7, 1974, now abandoned, which in turn a continuation-in-part application of application Ser. No. 313,431, filed Dec. 8, 1972, now U.S. Pat. No. 3,833,725, and 413,965, filed Nov. 8, 1973 now abandoned.

FIELD OF THE INVENTION

This invention relates to medicament preparations and vehicles therefor. In presently preferred embodiments, the present invention relates to medicament preparations wherein the chemical potency of the medicament is stabilized, for extended periods of time, by dispersing or dissolving the medicament in a dialkylated mono- or polyalkylene glycol vehicle optionally containing an antioxidant for the vehicle.

BACKGROUND OF THE INVENTION

The use of alkylene glycols or monoalkyl ethers thereof, either alone or in combination with other vehicle components, as carriers for medicaments, such as steroids or prostaglandins, is well-known. See, for example, Great Britain Pat. No. 1,133,800; South African Pat. No. 70/04245; and U.S. Pat. Nos. 2,600,344; 2,856,329; 3,069,322; 3,592,222; 3,592,930; and 3,673,213. Such carriers, however, do not, in general, provide requisite stabilizing properties for the medicament material. That is, after relatively short storage times, the chemical potency of the active medicament had degraded significantly to a point where the preparation, if taken at the recommended dosage level, might be of insufficient activity to accomplish the desired therapeutic objective.

Of particular interest in the present invention are the family of materials known as prostaglandins. Prostaglandins are a group of chemically related 20-carbon chain hydroxy fatty acids having the basic skeleton of prostanoic acids:

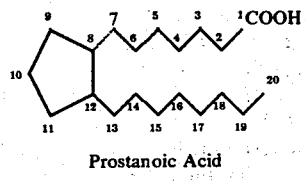

Prostanoic Acid

The prostaglandins having a hydroxy group at the C-11 position and a keto group at the C-9 position are known as the PGE series. Those having a hydroxyl group in place of the keto group at the C-9 position are known as the PGF series and are further designated by an α or β suffix to indicate the configuration of the hydroxyl group at the C-9 position. The natural compounds are the α-hydroxy substituted compounds. They may contain different degrees of unsaturation in the molecule, particularly at C-5, C-13, and C-17, the unsaturation is also indicated by a suffix. Thus, for example, $PGE_1$ refers to a prostanoic acid having a trans olefin bond at the 13-position. For a review on prostaglandins and the definition of primary prostaglandins, see, for example, S. Bergstrom, Recent Progress in Hormone Research 22, pp. 153–175 (1966) and S. Bergstrom, Science 157, page 382 (1967).

Using accepted nomenclature, prostaglandins of the PGE, PGF, PGA and PGB series are named as follows:

$PGE_1$: 11α,15α-dihydroxy-9-keto-13-prostenoic acid;

$PGE_2$: 11α,15α-dihydroxy-9-keto-5,13-prostadienoic acid;

$PGE_3$: 11α,15α-dihydroxy-9-keto-5,13-17-prostatrienoic acid;

$PGF_1$: 9α,11α,15α-trihydroxy-13-prostenoic acid;

$PGF_2$: 9α,11α,15α-trihydroxy-5,13-prostadienoic acid;

$PGA_1$: 15α-hydroxy-9-keto-10,15-prostadienoic acid;

$PGA_2$: 15α-hydroxy-9-keto-10,13,17-prostatrienoic acid;

$PGB_1$: 15α-hydroxy-9-keto-8,13-prostadienoic acid; and, $PGB_2$: 15α-hydroxy-9-keto-10,13,17-prostatrienoic acid.

Prostaglandins are widely distributed in mammalian tissues and have been isolated from natural sources in very small amounts. In addition a number of the natural occurring prostaglandins have been prepared by chemical synthesis; see for example, J. Am. Chem. Soc. 91, 5675 (1969), J. Am. Chem. Soc. 92, 2586 (1970), J. Am. Chem. Soc. 93, 1489–1493 (1971) and references cited therein, W. P. Schneider et al, J. Am. Chem Soc. 90, 5895 (1968), U. Axen et al., Chem. Commun., 303 (1969), and W. P. Schneider, Chem. Commun. 304 (1969).

Because of the remarkable range of biological and pharmacological properties exhibited by this family of compounds, a great deal of interest has focused upon such compounds. It is known, however, that prostaglandins in general, and specifically $PGE_2$, are, from a chemical point of view, relatively unstable. See, for example, Brummer J. Pharm. Pharmac. 23, 804 (1971), and Karim et al., European J. Pharmacol. 4, 416 (1968). It would, therefore, be desirable to have a prostaglandin preparation wherein the prostaglandin material is stabilized by the vehicle material.

OBJECTS OF THE INVENTION

It is the primary object of this invention to provide novel vehicles for medicament preparations.

It is a further object of this invention to provide novel vehicles for medicaments which, in addition to serving as a carrier for the medicament, stabilize for an extended period of time the chemical potency of the medicament.

It is a further object of this invention to provide dialkylated mono- and poly-alkylene glycols as vehicles for medicament preparations.

It is a further object of this invention to provide medicament preparations having a dialkylated mono- or poly-alkylene glycol as the vehicle therefor.

It is a further object of this invention to provide novel, substantially anhydrous pharmaceutical preparations containing a dialkylated mono- or poly-alkylene glycol as the vehicle and at least one prostaglandin material.

It is a further object of this invention to provide medicament preparations having dialkylated mono- or poly-alkylene glycols as the vehicle therefor, and where the chemical potency of the medicament material is stabilized for extended periods of time through use of such dialkylated glycol vehicle.

It is a further object of this invention to provide substantially anhydrous prostaglandin preparations wherein the chemical potency of the prostaglandin material is stabilized through use of a dialkylated mono- or poly-alkylene glycol as the vehicle for the preparation.

It is a further object of the present invention to provide a substantially anhydrous aspirin preparation where the chemical potency of the aspirin is stabilized through use of a dialkylated mono- or poly-alkylene glycol vehicle.

It is a further object of this invention to provide novel, substantially anhydrous pharmaceutical preparations containing a medicament material, a dialkylated mono- or poly-alkylene glycol as a vehicle for the medicament material, and at least one antioxidant for the glycol vehicle.

These and still further objects, features, and advantages of the present invention will become apparent upon consideration of the following detailed disclosure.

BRIEF SUMMARY OF THE INVENTION

The above and still further objects, features, and advantages of the present invention are achieved, in accordance therewith, by admixing a pharmaceutically active quantity of an active medicament material with a dialkylated mono- or poly-alkylene glycol optionally including an antioxidant for the glycol vehicle. In a specific embodiment, for example, the combination of $PGE_2$ with the dimethyl ether of polyethylene glycol 550 has exhibited a high degree of chemical stability after storage for an extended period of time above room temperature.

The dialkylated mono- or poly-alkylene glycol of the present invention can be represented by the following structural formula:

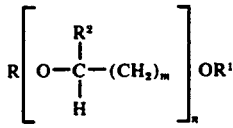

where R and $R^1$ are lower alkyl, $R^2$ is lower alkyl or hydrogen, $m$ is an integer from 1 to 6, and $n$ is an integer from 1 to a very large number, such as 500, such that the molecular weight of the glycol vehicle can be up to about 20,000 or so. The term poly-alkylene glycol is also intended to include those dialkylated glycols where the $[O — C(R^2)H—(CH_2)_m]$ units vary in the number of carbon atoms throughout the backbone of the polymer chain. For example, the term is intended to include dialkylated glycols having alternating ($O—CH_2—CH_2$) and ($O—CH_2—CH_2—CH_2$) units in the polymer chain. Other variations are possible, and, thusly, are intended to be included within the scope of the present invention.

As used in this specification, the term "lower alkyl" refers to both straight and branched chain alkyl groups having from 1 to 6 carbon atoms, such as, for example, methyl, ethyl, n-propyl, isopropyl, n-butyl, isobutyl, t-butyl, n-amyl, n-hexyl, and the like.

Illustrative dialkylated glycol vehicles include for example, 1,2-dimethoxyethane (ie, glyme), diglyme, triglyme, tetraglyme, polyethylene glycol-350-dimethyl ether, polyethylene glycol-550-dimethyl ether, polyethylene glycol-750-dimethyl ether, etc., where the numbers such as 350, 550 and 750, refer to the approximate average molecular weight of the polyethylene glycol vehicle. Depending upon the vehicle utilized and its molecular weight (or average molecular weight), the vehicle, and the corresponding pharmaceutical preparation will be liquids, semi-solids or waxes or solids at room temperatures. Blends of dialkylated glycols of different molecular weight are also contemplated for use in the present invention. As more fully described below, the pharmaceutical preparations of the present invention may take on a variety of dosage forms.

The dialkylated glycols of lower molecular weight (ie, glyme, diglyme, triglyme and tetraglyme) are known materials. The dialkylated glycols of higher molecular weight, on the order of about 350 to about 20,000, however, are considered to be novel materials. They are useful, as set forth herein, as vehicles for pharmaceutical preparations.

The dialkylated mono- or poly-alkylene glycols of the present invention are satisfactory carriers for a wide variety of active medicament materials, as will be shown below, and, in addition, have been shown to stabilize the chemical potency or activity of four distinct medicaments, ie, $PGE_2$, aspirin, oleic acid diethanolamide, and chloramiphenicol, an antibiotic. The dialkylated glycol vehicle, however, is, itself, subject to undesirable oxidation and, preferably, should include a minor amount, generally about 0.01 to about 1.0%, of one or more antioxidants to protect the chemical stability of the vehicle itself. The antioxidant can be eliminated if the pharmaceutical preparation is otherwise stable for the desired or requisite period of time. Exemplary antioxidants include propyl gallate, vitamin E, hydroquinone, hydroxycomarins, ethanolamine, lecithin, cephalin, ascorbic acid, malic acid, sorbitol, phosphoric acid, thiodipropionic acid and its esters, dithiocarbamates, butylated hydroxyanisole (BHA), and butylated hydroxytoluene (BHT), with a 50—50 mixture (by weight) of butylated hydroxyanisole and butylated hydroxytoluene presently being preferred.

In addition, the dialkylated glycol vehicle should be as pure as is technically or economically feasible. In particular, it should be substantially devoid of perioxides and/or other oxidation products thereof which tend, in the quantities present in the vehicle, to interfere with its vehicle and/or stabilizing properties.

The dialkylated glycol material can be prepared by alkylating both terminal hydroxy groups of an appropriate precursor (for example, a polyethylene glycol having a molecular weight of about 325 or 725). This is achieved by treating the precursor with sodium metal and then reacting the resultant reaction mixture with an alkyl halide, such as methyl iodide or methyl chloride, and separating, according to conventional techniques, the desired dialkylated glycol product.

The medicament which can be utilized in the preparations of the present invention include therapeutic agents for topical application including antibiotics such as tetracycline, oxytetracycline, chlortetracycline, chloramiphenicol, gramicidin, candicidin, nystatin and the like; anesthetics such as benzocaine, xylocaine, and the like; analgesics such as aspirin, 2-(6-methoxy-2-naphthyl)propionic acid, and the like; steroids having anti-inflammatory or other beneficial activity, such as 6α,9α-difluoro-11β-hydroxy-16α,17α-isopropylidenedioxy-pregna-1,4-diene-3,20-dione, 9α,11β,21-trichloro-6α-fluoro-16α,17α-isopropylidenedioxy-pregna-1,4-diene-3,20-dione, and those described in U.S. Pat. No. 3,592,930 which partial disclosure is incorporated herein by reference, and the like; naturally occurring or synthetic prostaglandins, such as $PGE_2$, $PGF_{2\alpha}$, the other prostaglandins referred to above, and the like; palmitic acid diethanolamide, oleic acid diethanolamide; antihistamines; antibacterials and fungicides; etc.

Incorporation of the medicament into the vehicle is in accordance with standard techniques and practices common to the pharmaceutical field, for example as described in Remington's Practice of Pharmacy, 12th Edition by Martin and Cook, Mach Publishing Company (1961). In certain instances, for example in pharmaceutically formulating $PGE_2$ mixtures with the vehicles of this invention, it may be desirable to conduct such formulation under nitrogen or non-oxidizing atmosphere to exclude oxygen which may have an adverse affect on the long-term stability of the resultant formulations.

The ratio of medicament to the dialkylated glycol vehicle can vary, depending upon the concentration of the medicament desired in the final unit dosage form. In general, however, the preparation should contain a pharmaceutically effective amount of the medicament, generally about 0.001–10%, with the balance being substantially the dialkylated glycol vehicle. In formulating the preparation, care should be taken to select a method which substantially eliminates water from the preparation so as to make it substantially anhydrous. Methods which do not substantially eliminate water are not desirable since water retention in the preparation will result in reduced activity or potency of the preparation over an extended period of time. Retention or uptake of a minimum amount of water, up to about 5%, is for all practical purposes, unavoidable and, therefore, not undesirable. It is preferred, however, to maintain the amount of residual water at the lowest practical level and certainly at a level which does not diminish the advantages afforded by the present invention.

As indicated above, the present invention is applicable to the use of a great variety of medicament materials as the pharmaceutically active component of the preparations of the present invention, such as, for example, the naturally occurring or synthetic prostaglandins specifically set forth above. It has been shown that the vehicle of this invention has stabilizing properties with respect to certain medicaments. Certain of such medicaments, including certain medicaments. Certain of such medicaments, including certain prostaglandins, are more stable than other medicaments and, to the extent that they are more stable, the stabilizing effect of the dialkylated glycol vehicle may be correspondingly diminished. The combination of the dialkylated glycol vehicle and a relatively stable medicament is, nonetheless, considered to be within the scope of the present invention. To the extent that the particular medicament is relatively chemically unstable, as for example is $PGE_2$, the dialkylated glycol vehicle has been found to enhance the chemical stability of the medicament during long periods of storage at or above room temperature.

The final preparation should have a pH, or be adjusted to a pH, which provides for optimum stability for a given active component. For example, the pH of a $PGE_2$ formulation should be adjusted to about 4–5 (as determined from a 10% aqueous solution of the formulation) if the formulation is to have extended stability. pH adjustment can be made with any suitable acid or base, for example, citric acid, acetic acid, benzoic acid, hydrochloric acid, phosphoric acid, and the like.

Either at the time of initial production of the preparation of the present invention, or at some time subsequent thereto, the preparation can be formulated into a variety of pharmaceutical or veterinary compositions and, as such, can be administered in a wide variety of dosage forms suitable for enteral, parenteral, or topical administration. Such compositions may have a single medicament as the sole active component or a combination of pharmaceutically compatible medicaments may be utilized. The preparation is, thus, typically administered as a pharmaceutical composition containing the pharmaceutically active medicament(s) and/or a pharmaceutically acceptable salt thereof, the dialkylated glycol vehicle, and, optionally, one or more non-toxic antioxidants for the glycol vehicle. If desired, additional carrier or adjuvants may be utilized in preparing the pharmaceutical compositions. The administerable pharmaceutical composition may take the form of creams, ointments, oral or vaginal tablets, rectal or vaginal suppositories, encapsulated preparations, bougies, food premixes, of the like, preferably in unit dosage forms for simple administration of precise dosages. Since the vehicles of this invention are generally liquids or semi-solids, depending upon the molecular weight thereof, creams, ointments, suppositories and solutions are the preferred administration forms. Auxiliary non-toxic solid carriers which can be used in conjunction with the dialkylated glycol vehicle for tablet preparations include, for example, pharmaceutical grades of mannitol, lactose, starches, magnesium stearate, sodium saccharin, talcum, sodium bisulfite, and the like. Liquid pharmaceutically administerable compositions can, for example, be formulated by utilizing a liquid dialkylated glycol vehicle to thereby form a solution. A liquid concentrate can be prepared by admixing a medicament in a quantity greater than that intended to be eventually administered with a liquid dialkylated glycol material. Prior to use, the concentrate is diluted to the desired medicament concentration, for example, as by mixing with further dialkylated glycol or sterile saline. If desired, the pharmaceutical composition to be administered may also contain minor amounts of non-toxic auxiliary substances such as wetting or emulsifying agents, pH buffering agents, and the like, for example, sodium acetate, sorbitan monolaurate, triethanolamine oleate, etc. Actual methods of preparing such dosage forms are known, or will be apparent, to those skilled in this art.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLES I–XIV

The solubility (expressed as mg. medicament per ml. of vehicle) at 30° C of 14 different medicaments in polyethylene glycol-550-dimethyl ether is given in the following table:

TABLE I

| Ex. | Medicament | Solubility, (mg./ml.) |
|---|---|---|
| I | 6α,9α-difluoro-11β-hydroxy-16α,17α-isopropylidenedioxy-pregna-1,4-diene-3,20-dione | 6.5 |
| II | 9α,11β,21-trichloro-6α-fluoro-16α,17α-isopropylidenedioxy-pregna-1,4-diene-3,20-dione | 1.5 |
| III | $PGE_2$ | 2.0 |
| IV | $PGF_{2\alpha}$ | 36.0 |
| V | palmitic acid diethanolamide | 2.7 |
| VI | 2-(6-methoxy-2-naphthyl)propionic acid | 50.0 |
| VII | aspirin (acetylsalicylic acid) | 120.0 |
| VIII | benzocaine | 111.0 |
| IX | xylocaine | 57.0 |
| X | chloramphenicol | 70.0 |
| XI | gramicidin | 4.4 |
| XII | tetracycline | 125.0 |
| XIII | oxytetracycline hydrochloride | 0.34 |
| XIV | chlortetracycline hydrochloride | 0.416 |

EXAMPLE XV

A formulation is prepared having 0.5 g. aspirin and 0.05% BHA per 1.0 g. polyethylene glycol-750-dimethyl ether, and stored at 80° C. Decomposition of the aspirin is measured vs. time. The time for 10% decomposition is 27 hours. This reflects approximately a 30 month shelf-life at 25° C. This can be compared to a published report[Jun et al., J. Pharm. Sec. Vol.61,1160(1972)] which indicates that the time for 10% decomposition of aspirin in several polyethylene glycols at 80° C is 2 hours reflecting a shelf-life at 25° C. of only 3.5 months.

EXAMPLE XVI

A formulation is prepared having 1 mg. $PGE_2$ per ml. 1,2-dimethoxyethane. After 12 days storage at 60° C. under a nitrogen atmosphere, the $PGE_2$ assays 100% of its initial activity.

EXAMPLE XVII

A formulation is prepared having 1 mg. $PGE_2$ per ml. of triethylene glycol-dimethyl ether. After 5 days storage at 60° C. under a nitrogen atmosphere, the $PGE_2$ assays 100% of its initial activity.

EXAMPLES XVIII–XXV

The following formulations are prepared having 1 mg. $PGE_2$ per ml. of polyethylene glycol-550-dimethyl ether, and the additional material(s) as set forth below. The percent activity of the $PGE_2$ after storage for 7 days at 80° C. is also given.

| Example | Additional Material(s) | Activity |
|---|---|---|
| XVIII | 0.05% citric acid, 0.025% BHA, and 0.025% BHT (sealed under air) | 99% |
| XIX | Same as XVIII, except sealed under nitrogen | 91% |
| XX | Same as XVIII, except 0.1% citric acid | 82% |
| XXI | Same as XX, except sealed under nitrogen | 86% |
| XXII | Same as XVIII | 87% |
| XXIII | Same as XIX | 87% |
| XXIV | 0.05% citric acid and 0.05% BHA (sealed under air) | 81% |
| XXV | Same as XXIV, except sealed under nitrogen | 99% |

EXAMPLE XXVI

A formulation is prepared having 1 mg. $PGE_2$, 0.01% edetic acid, 0.01% BHA and 0.01% BHT per ml. polyethylene glycol-550-dimethyl ether, and sealed in an ampule under nitrogen atmosphere. After 18 days storage at 80° C., the $PGE_2$ assays 100% of its initial activity.

EXAMPLES XXVII–XXIX

The following formulations are prepared having 1 mg. $PGE_2$ per ml. polyethylene glycol-550-dimethyl ether, and the additional material(s) as set forth below, and then sealed in individual ampules under nitrogen atmosphere. The time ($t_{90}$) for 10% of the $PGE_2$ to decompose when stored at 80° C. is given. Also given is the corresponding $t_{90}$ for a formulation having 1 mg. $PGE_2$ per ml. polyethylene glycol-400, also sealed under nitrogen atmosphere.

| Example | Additional Material(s) | $t_{90}$ |
|---|---|---|
| — | ($PGE_2$ in PEG 400) | 20 hours |
| XXVII | 0.1% citric acid | 7.1 days |
| XXVIII | 0.01% citric acid | 8.8 days |
| XXIX | 0.01% BHA, 0.01% BHT, and 0.01% EDTA | undecomposed after 18 days |

By comparison, 1 mg. $PGE_2$ and 1 ml. polyethylene glycol 400 assays 54% $PGE_2$ activity after storage for two months at 45° C.; 0.2 mg. $PGE_2$ in 2.7598 g. polyethylene glycol 4,000 assays 70% $PGE_2$ activity after storage for 6 months at room temperature and 72% $PGE_2$ activity after storage for 3 months at 45° C.; a suppository of 0.2 mg. $PGE_2$ in 2.7298 g. base comprising 2% polyethylene glycol 4,000 and 98% polyethylene glycol 1,000 assays 62% $PGE_2$ activity after storage for six months at room temperature; a formulation of $PGE_2$ in polyethylene glycol 400 assays 73% $PGE_2$ activity after 4 months at room temperature; and a formulation of $PGE_2$ in polyethylene glycol 4000 assays 82% $PGE_2$ activity after 5 months at room temperature.

EXAMPLE XXX

A formulation is prepared containing 1 mg. $PGE_2$ per ml. of the diethyl ether of polyethylene glycol-750, and 0.025% BHA and 0.025% BHT.

EXAMPLE XXXI

A formulation is prepared having 1 mg. $PGE_2$ per ml. of the dipropylether of polyethylene glycol-550, and 0.025% BHA and 0.025% BHT.

EXAMPLE XXXII

A formulation is prepared having 1 mg. $PGE_2$ per ml. of the dimethyl ether of propylene glycol, and 0.025% BHA and 0.025% BHT.

EXAMPLE XXXIII

A formulation is prepared having 2 mg. of oleic acid diethanolamide per ml. of 1,2-dimethoxyethane containing 0.025% BHT and 0.025% BHA. After 5 weeks at 80° C., the oleamide assays 96% of its initial activity. This reflects approximately 3–4 years shelf time at 25° C. In vitro, this compound inhibits lipase and, thus, may have utility as an anti-acne preparation.

EXAMPLE XXXIV

A formulation is prepared having 100 mg. of aspirin per ml. of polyethylene glycol-350-dimethyl ether, sealed in an ampoule under air, and stored at 80° C. The time for 10% decomposition ($t_{90}$) is 24 hours. This reflects approximately a 30 month shelf-life at 25° C. Thus, this Example describes the preparation of a liquid aspirin formulation which is stable for long periods of time at or about room temperature.

EXAMPLE XXXV

A formulation is prepared having 5 mg. of palmitic acid diethanolamide per ml. of polyethylene glycol-350-dimethyl ether, sealed in an ampoule under air, and stored at 80° C. The formulation remains undecomposed after 14 days. The same result is attained with a formulation which additionally contains 0.05% BHA.

EXAMPLE XXXVI

A formulation is prepared having 0.5 mg. of chloramphenicol per ml. of polyethylene glycol-350-dimethyl ether, and 0.05% BHA, sealed in an ampoule under air, and stored at 80° C. After 2 and 5 days storage, the chloramphenicol assays 95 and 66%, respectively, of its initial activity at time zero. This reflects a shelf-life at room temperature of at least 1 year. By comparison when polyethylene glycol 400 is utilized in place of the dialkylated vehicle, the chloramphenicol assays 50% and less than 20% after 2 and 5 days, respectively, at 80° C.

EXAMPLE XXXVII

A formulation is prepared having 0.5 mg. of nystatin per ml. of polyethylene glycol-350-dimethyl ether, and 0.05% BHA, sealed in an ampoule under air, and stored at 80° C. After 2 and 5 days storage, the nystatin assays 56% and less than 40%, respectively, of its initial activity at time zero. By comparison, when polyethylene glycol 400 is utilized in place of the dialkylated vehicle, there is total decomposition (ie, loss of activity) after only 2 days at 80° C. Thus, the polyethylene glycol-350-dimethyl ether has a significant stabilizing effect on nystatin when compared to polyethylene glycol 400.

It can thus be seen (from Examples Xv–XXIX and XXXIII–XXXVI hereof) that the incorporation of aspirin, oleic or palmitic acid diethanolamide, chloramphenicol, or a prostaglandin material, particularly $PGE_2$, into the dialkylated glycol vehicle of the present invention stabilizes, for an extended period of time, the chemical potency of the particular medicament.

For a discussion of the significance of the data presented herein, and the extrapolation thereof to shelf-lives at room temperature, reference should be made, for example, to Kennon, "Use of Models in Determining Chemical Pharmaceutical Stability", J. of Pharm. Sciences, 53, 815–818 (July, 1964).

EXAMPLE XXXVIII

A cream-like formulation is prepared having 1.0% tetracycline hydrochloride, 79.0% polyethylene glycol-350-dimethyl ether (including 0.05% BHA), and 20.0% polyethylene glycol-6000-dimethyl ether (also including 0.05% BHA), sealed in epoxy-lined aluminum tubes under air, and stored at 45° C. After 4 months storage the tetracycline hydrochloride assays 98% of its initial activity at time zero. In vitro human skin penetration studies on a labeled ($H^3$) tetracycline hydrochloride cream-like preparation having the above composition show equivalent skin penetration versus a first formulation comprising 0.5% tetracycline hydrochloride in 75% propylene glycol (a saturated solution) and a second formulation comprising 0.05% tetracycline hydrochloride in a pH 6.6 buffer (also a saturated solution). Both of the latter formulations are, however, highly unstable such that the tetracycline activity degrades rapidly with less than 50% active remaining after two weeks storage at room temperature.

EXAMPLE XXXIX

A cream-like formulation is prepared having 1.0% oxytetracycline hydrochloride, 79.0% polyethylene glycol-350-dimethyl ether (including 0.05% BHA), and 20.0% polyethylene glycol-6000-dimethyl ether (also including 0.05% BHA), sealed in epoxy-lined aluminum tubes under air, and stored at 45° C. After 2 months storage, the oxytetracycline hydrochloride assays 92% of its initial activity at time zero, while after 4 months storage it assays 75% of its initial activity. After 3 months storage at 37° C, the oxytetracycline hydrochloride also assays 92% of its initial activity.

EXAMPLE XL

A cream-like formulation is prepared having 1.0% chlortetracycline hydrochloride, 79.0% polyethylene glycol-350-dimethyl ether (including 0.05% BHA), and 20.0% polyethylene glycol-6000-dimethyl ether (also including 0.05% BHA), sealed in epoxy-lined aluminum tubes under air, and stored at 45° C. After 4 months storage, the tetracycline hydrochloride assays 100% of its initial activity at time zero.

It can thus be seen from Examples XXXVIII–XL that the incorporation of tetracycline hydrochloride, oxytetracycline hydrochloride or chlortetracycline hydrochloride into the dialkylated glycol vehicle of the present invention stabilizes, for an extended period of time, the chemical potency of the tetracycline medicament. Although the tetracyclines are not completely solubilized in the formulation, good release and skin penetration characteristics are, nonetheless, obtained. The formulations are of cream-like, cosmetically acceptable consistency and are intended for use in the treatment of acne.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A stabilized, antibiotic composition comprising a major amount of at least one dialkylated mono- or poly-alkylene glycol having the formula:

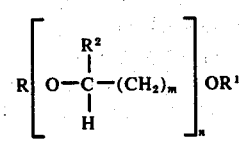

where R and R[1] are independently lower alkyl having 1 to 6 carbon atoms, R[2] is hydrogen or lower alkyl having 1 to 6 carbon atoms, $m$ is an integer from 1 to 6, and $n$ is an integer from 1 to a very large number such that the molecular weight of said dialkylated glycol is up to about 20,000 and a pharmaceutically effective amount of a tetracycline or a pharmaceutically acceptable salt thereof, said composition containing a minimum amount of water, up to about 5%, and being substantially devoid of peroxides and other oxidation products in quantities which interfere with the carrier or stabilizing properties of said composition.

2. The composition of claim 1 wherein R and R[1] are methyl.

3. The composition of claim 1 wherein R and R[1] are methyl, and R[2] is hydrogen.

4. The composition of claim 1 wherein said dialkylated glycol is selected from the group consisting of the dimethyl ether of polyethylene glycol, the dimethyl ether of triethylene glycol, glyme, diglyme, triglyme, and tetraglyme.

5. The composition of claim 1 wherein said dialkylated glycol is a diamethyl ether of a polyethylene glycol.

6. The composition of claim 1 wherein said dialkylated glycol is a mixture of dimethyl ethers of polyethylene glycols having different molecular weights.

7. The composition of claim 1 wherein said tetracycline is selected from the group consisting of tetracycline, oxytetracycline and chlortetracycline, and the pharmacutically acceptable salts thereof.

8. The composition of claim 1 further including a minor amount of at least one antioxidant for said dialkylated glycol material.

9. The composition of claim 8 wherein said antioxidant is selected from the group consisting of propyl gallate, vitamin E, butylated hydroxyanisole, butylated hydroxy-toluene, and mixtures thereof.

10. The composition of claim 8 wherein said composition includes about 0.01% to about 1.0% of said antioxidant.

11. A stabilized, antibiotic composition comprising a major amount of a dialkylated mono- or poly-alkylene glycol having the formula:

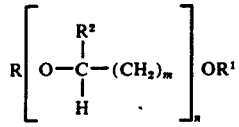

where R and R[1] and independently lower alkyl having 1 to 6 carbon atoms, R[2] is hydrogen or a lower alkyl having 1 to 6 carbon atoms, $m$ is an integer from 1 to 6, and $n$ is an integer from 1 to a very large number such that the molecular weight of said dialkylated glycol is up to about 20,000; a pharmaceutically effective amount of a tetracycline or a pharmaceutically acceptable salt thereof; and a minor amount of at least one antioxidant for said dialkylated glycol material; said composition containing a minimum amount of water, up to about 5%, and being substantially devoid of peroxides and other oxidation products in quantities which interfere with the carrier or stabilizing properties of said glycol material.

12. The composition of claim 11 wherein R and R[1] are methyl, and R[2] is hydrogen.

13. The composition of claim 11 wherein said dialkylated glycol has a molecular weight from about 350 to about 750.

14. The composition of claim 11 wherein said dialkylated glycol is selected from the group consisting of the dimethyl ether of polyethylene glycol, the dimethyl ether of triethylene glycol, glyme, diglyme, triglyme, and tetraglyme.

15. The composition of claim 11 wherein said tetracycline is selected from the group consisting of tetracycline, oxytetracycline and chlortetracycline, and the pharmaceutically acceptable salts thereof.

16. The composition of claim 11 wherein said composition includes about 0.01 to about 1.0% of said antioxidant selected from the group consisting of propyl gallate, vitamin E, butylated hydroxyanisole, butylated hydroxytoluene, and mixtures thereof.

17. The composition of claim 11 wherein said dialkylated glycol is a mixture of dimethyl ethers of polyethylene glycols of different molecular weights.

18. The composition of claim 17 wherein said mixture comprises a dimethyl ether of polyethylene glycol having a molecular weight of 350 and a dimethyl ether of polyethylene glycol having a molecular weight of 6000.

19. The composition of claim 18 wherein said tetracycline is chlortetracycline.

20. The method of controlling acne which comprises topically applying to an acne affected skin area a composition comprising a major amount of a dialkylated mono- or poly-alkylene glycol, having the formula:

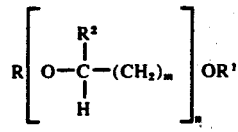

where R and R[1] are independently lower alkyl having 1 to 6 carbon atoms, R[2] is a hydrogen or lower alkyl having 1 to 6 carbon atoms, $m$ is an integer from 1 to 6, and $n$ is an integer from 1 to a very large number such that the molecular weight of said dialkylated glycol is up to about 20,000; an acne controlling amount of a tetracycline; and a minor amount of at least one antioxidant for said dialkylated glycol material, said composition containing a minimum amount of water, up to about 5%, and being substantially devoid of peroxides and other oxidation products in the quantities which interfere with the carrier or stabilizing properties of said glycol material.

21. The method of claim 20 wherein said tetracycline is selected from the group consisting of tetracycline, oxytetracycline and chlortetracycline, and the pharmaceutically acceptable salts thereof.

22. The method of claim 21 wherein said dialkylated glycol is a mixture of the dimethyl ethers of polyethylene glycols of different molecular weight.

23. The method of claim 21 wherein said dialkylated glycol is the dimethyl ether of polyethylene glycol.

* * * * *